United States Patent [19]

Binder

[11] Patent Number: 4,801,591

[45] Date of Patent: Jan. 31, 1989

[54] 2-ALKENYLENE-THIENO-1,2-THIAZOLE DERIVATIVES WITH LIPID-LOWERING ACTIVITY

[75] Inventor: Dieter Binder, Vienna, Austria

[73] Assignee: Chemie-Linz Aktiengesellschaet, Linz, Austria

[21] Appl. No.: 876,673

[22] Filed: Jun. 19, 1986

[30] Foreign Application Priority Data

Jul. 4, 1985 [AT] Austria .................. 1988/85

[51] Int. Cl.$^4$ .................. C07D 513/04; A61K 31/425
[52] U.S. Cl. .................. 514/373; 548/209; 548/210
[58] Field of Search .............. 514/373; 548/207, 209, 548/210

[56] References Cited

U.S. PATENT DOCUMENTS

2,957,883 10/1960 Novello ........................ 548/210
4,563,474 1/1986 Franke et al. ................ 514/373

FOREIGN PATENT DOCUMENTS

48-24735 7/1973 Japan .................. 548/210
49-20779 5/1974 Japan .................. 548/210
53-32118 3/1978 Japan .................. 514/373

OTHER PUBLICATIONS

Abstract for Japan Patent #48-24735 (7/24/73).
Abstract for Japan Patent #49-20779 (5/27/74).
Abstract for Japan Patent #53-32118 (3/27/78).
*Organic Chemistry*, by Morrison and Boyd, (Allyn & Bacon Publ.), (2nd ed.), pp. 582–583 (1966).
*Modern Synthetic Reactions* by House, (W. A. Benjamin, Publ.), pp. 170–171 (1965).
"Biotransformation von Arzneimitteln" by Pfeifer et al., vol. 5, p. 442 and vol. 4, p. 146 (1981).

*Primary Examiner*—Donald G. Daus
*Assistant Examiner*—E. Bernhardt
*Attorney, Agent, or Firm*—Wenderoth, Lind & Ponack

[57] ABSTRACT

The invention relates to new thieno-1,2-thiazole derivatives of the formula

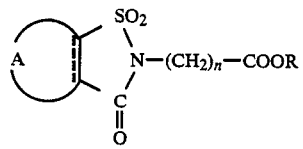

wherein A, with the two carbon atoms of the thiazole ring, forms a group of the formula

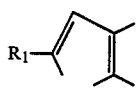

IIa

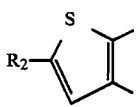

IIb or

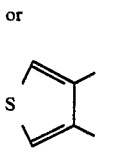

IIc and the broken line indicates the double bond present in the thieno structures of the formulae IIa and IIb, n denotes the integer 2, 3 or 4, R denotes hydrogen or lower alkyl, $R_1$ denotes hydrogen, lower alkyl, halogen, trifluoromethyl, lower alkoxy or lower alkylthio and $R_2$ denotes hydrogen, lower alkyl or halogen; and the pharmaceutically acceptable salts of compounds of the formula I wherein R denotes hydrogen, a process for their preparation, pharmaceutical products containing these compounds, and their use in medicaments. The compounds of the formula I and salts thereof have a lipid-lowering action.

6 Claims, No Drawings

2-ALKENYLENE-THIENO-1,2-THIAZOLE DERIVATIVES WITH LIPID-LOWERING ACTIVITY

The invention relates to new thieno-1,2-thiazole derivatives of the formula

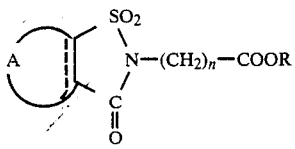

wherein A, with the two carbon atoms of the thiazole ring, forms a group of the formula

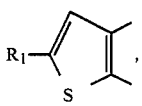

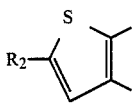

or

and the broken line indicates the double bond present in the thieno structures of the formulae IIa and IIb, n denotes the integer 2, 3 or 4, R denotes hydrogen or lower alkyl, $R_1$ denotes hydrogen, lower alkyl, halogen, trifluoromethyl, lower alkoxy or lower alkylthio and $R_2$ denotes hydrogen, lower alkyl or halogen; and the pharmaceutically usable salts of compounds of the formula I wherein R denotes hydrogen, a process for their preparation, pharmaceutical products containing these compounds, and their use in medicaments.

The expression "lower alkyl" used in this description designates straight-chain or branched saturated hydrocarbon radicals with 1 to 4 carbon atoms, such as, for example, methyl, ethyl, propyl, isopropyl, butyl, isobutyl, sec.-butyl or tert.-butyl (1,1-dimethylethyl). The expression "lower alkox)" represents an alkyl ether group in which the alkyl radical has the above meaning, for example methoxy, ethoxy, propoxy, isopropoxy, butoxy, isobutoxy, sec.-butoxy or tert.-butoxy, and the designation "lower alkylthio" represents an alkylthio ether group with the abovementioned meaning for the alkyl radical, such as methylthio, ethylthio, propylthio, isopropylthio, butylthio, isobutylthio, sec.-butylthio or tert.-butylthio. The term "halogen" designates chlorine, bromine, fluorine or iodine.

In a preferred class of compounds of the formula I, n denotes the number 2 or 3, the number 2 being particularly preferred. R preferably represents hydrogen, 1,1-dimethylethyl or ethyl, R again particularly preferably denoting hydrogen.

In another preferred class of compounds of the formula I, A denotes the thieno group of the formula IIc. In compounds of the formula I wherein A represents a group of the formula IIa, $R_1$ preferably represents hydrogen, and in compounds of the formula I wherein A denotes a group of the formula IIb, $R_2$ is preferably hydrogen or chlorine.

The thieno-1,2-thiazole derivatives of the formula I and salts thereof are prepared, according to the invention, by methods which are known per se, preferably by a process in which (a) a compound of the formula

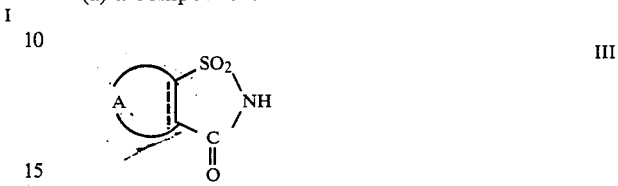

wherein A has the meaning given in the case of formula I, is converted into its alkali metal salt and this is reacted with a compound of the formula

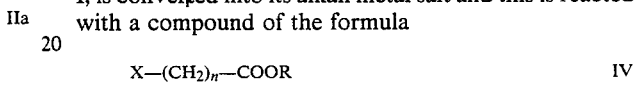

wherein n and R have the meaning given in the case of formula I and X represents a reactive leaving group, after which (b) if appropriate, a compound of the formula I thus obtained, wherein R denotes 1,1-dimethylethyl, is converted into a compound of the formula I wherein R denotes hydrogen by heating in a solvent which is inert in the reaction, in the presence of catalytic amounts of a strong acid, and (c) if desired, a free acid of the formula I obtained in process step (a) or (b), wherein R denotes hydrogen, is converted into a pharmaceutically acceptable salt with inorganic or organic bases.

The anhydrous alkali metal salts of compounds of the formula III can be prepared in the customary manner, for example by treating a compound cf the formula III with calculated amounts of aqueous alkali metal hydroxide solution, preferably sodium hydroxide solution or potassium hydroxide solution, or with the calculated amount of an alcoholic alkali metal alcoholate solution, preferably an alcoholic sodium methylate, sodium ethylate or potassium ethylate solution, and obtaining the alkali metal salts in the dry residue by evaporating the resulting solution.

The alkali metal salts for the process according to the invention can also be prepared in situ in a particularly simple and advantageous manner by adding the calculated amount of sodium hydride, for example a sodium hydride suspension in white oil, to a solution of the compound of the formula III in an aprotic polar solvent, which can also be used in the subsequent reaction of the alkali metal salt with a compound of the formula IV, for example in dimethylformamide, dimethyl sulfoxide, dimethyl acetamide, hexamethylphosphoric acid triamide and the like.

The leaving group designated by the symbol X in formula IV is preferably a halogen atom which can easily be split off, such as chlorine, bromine or iodine, or an sulfonic acid ester group. such as tosyloxy or mesyloxy, or the like.

The reaction of the alkali metal salts of compounds of the formula III with the compounds of the formula IV by process step (a) can be carried out in the presence or absence of a solvent which is inert in the reaction. The reaction is advantageously carried out in a polar aprotic solvent in which the alkali metal salts are readily soluble, the solvents mentioned above for the preparation of the alkali metal salts being preferably suitable. The reaction is preferably carried out by warming, temperatures of 80° to 140° C. with a temperature optimum at about 100° C. being particularly preferred. Depending on the reaction temperature and the reactivity of the particular reaction partners employed, in particular on the nature of the leaving group X, the reaction time is between a few hours and several days.

The tert.-butyl esters of the formula I obtained in this reaction, in which R represents a 1,1-dimethylethyl radical, can, if desired, be converted into the free acids of the formula I wherein B denotes hydrogen by process step (b). The 1,1-dimethylethyl group is advantageously split off in the form of isobutylene to form the free carboxyl group by dissolving the starting compound of the formula I (R=1,1-dimethylethyl) in an aprotic solvent which is inert in the reaction, preferably an aromatic hydrocarbon, such as benzene, toluene or xylene, and heating the solution in the presence of catalytic amounts of a strong acid. Strong acids which are partly or completely soluble in the solvents mentioned, for example benzenesulfonic acid, p-toluenesulfonic acid, methanesulfonic acid and the like, are preferably used for this purpose. The reaction temperature at which the splitting off of the 1,1-dimethylethyl group is carried out can be chosen virtually as desired within a wide temperature range above room temperature, the reflux temperature of the reaction mixture having proved to be particularly advantageous.

The reaction time depends on the reaction temperature and is, for example, about 90 minutes when the reaction mixture in toluene is heated under reflux. Compounds of the formula I obtained in the reactions in process step (a) or (b) which have a free carboxyl group can be converted into their pharmaceutically usable salts in the customary manner with inorganic or organic bases. The salt formation can be carried out, for example, by dissolving the compounds mentioned of the formula I (R=H) in a suitable solvent, for example water or a lower aliphatic alcohol, adding an equivalent amount of the desired base, ensuring thorough mixing and, when salt formation has ended, distilling off the solvent in vacuo. If appropriate, the salts can be recrystallized after isolation.

Examples of pharmaceutically usable salts are metal salts, in particular alkali metal or alkaline earth metal salts, such as sodium, potassium, magnesium or calcium salts. Other harmaceutically usable salts are, for example, also ammonium salts which readily crystallize. The latter are derived from ammonia or organic amines, for example mono-, di- or tri-lower (alkyl, cycloalkyl or hydroxyalkyl)-amines, lower alkylene diamines or (hydroxylower alkyl or aryl-lower alkyl)-lower alkylammonium bases, for example methylamine, diethylamine, triethylamine, dicyclohexylamine, triethanolamine, ethylenediamine, tris(hydroxymethyl)-aminomethane, benzyl-trimethylammonium hydroxide and the like.

The starting compounds of the formula IV are known from the literature. The starting compounds of the formula III used for the process according to the invention are either likewise known from the literature (German Offenlegungsschrift Nos. 2,534,689, 2,839,266 and 2,749,640), or they can be prepared in a manner which is known per se, starting from known products. In particular, they can be synthesized in accordance with the following equation by customary chemical methods of working with which any expert is familiar.

The starting compounds of the formulae V and VII shown in the equation are known from the literature (German Offenlegungsschrift Nos. 2,537,070, 2,835,760, 2,838,851, and European Patent No. A-103,142). Unless stated otherwise, A, $R_1$ and $R_2$ in the following equation have the meaning given in the case of formula I.

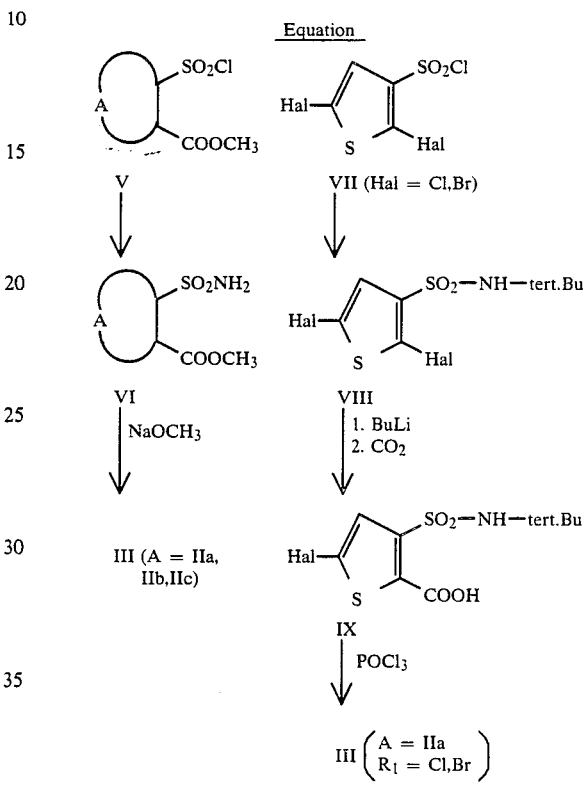

The compounds of the formula I and their pharmaceutically usable salts show useful pharmacological properties in animal experiments. In particular, they effect a marked reduction in the blood level values of cholesterol and triglycerides and, on the basis of these lipid-lowering properties, can be used in human medicine for the treatment and prophylaxis of diseases caused by an increased level of cholesterol and/or triglycerides in the blood. Such diseases are primarily cardiovascular disorders, inter alia thrombosis, arteriosclerosis, myoardial infarction and angina pectoris. These actions can be demonstrated by in vitro experiments or in vivo animal experiments, preferably on mammals, for example guineapigs, mice, rats, cats, dogs or monkeys. The compounds mentioned can be administered to these animals enterally or parenterally, and in view of human administration in particular also orally.

The following test method, inter alia, is used to investigate the lipid-lowering properties of compounds of the general formula I.

The test substances are suspended in each case in freshly prepared 1% strength carboxymethylcellulose and are administered intraperitoneally once daily in constant doses of 20 mg/kg with a unit administration volume of 10 ml/kg over a period of 14 days to male mice (strain: OF 1, Swiss, SPF; weight at the start of the experiment: about 25 g) which have free access to a standard diet and drinking water. The control group receives only 10 ml/kg of 1% strength carboxymethylcellulose.

4 hours after the last administration of the test substances or of the carboxymethylcellulose, in the control group, the animals are sacrificed by exsanguination via the aorta carotis. EDTA (ethylenediaminetetraacetic acid) plasma is obtained from the test animals to determine the blood level values of lipids.

ANALYTICAL METHODS

Cholesterol is determined both by the conventional method (Liebermann-Burchard color test; Zbl. Pharm, 124 (7), 396 et seq.) and by a completely enzymatic method (Celichrome cholesterol; test system: Chemie Linz AG, Diagnostica; Linz, Austria).

The triglycerides are determined completely enzymatically (Triglyceride iodonitrotetrazolium violet; test system: Chemie Linz AG, Diagnostica; Linz, Austria).

In this test, compounds of the general formula I exhibit powerful lipid-lowering properties. For example, 2,3-dihydro-3-oxo-thieno(3,4-d)-1,2-thiazole-propionic acid 1,1-dioxide at a dosage of 20 mg/kg intraperitoneally effects a 9.2% reduction in the blood level value of cholesterol and a 7.8% reduction in the blood level value of triglycerides in comparison with the control group.

The compounds of the general formula I can be used as medicines, for example in the form of pharmaceutical products which contain them mixed with a pharmaceutical organic or inorganic inert auxiliary and/or excipient suitable for enteral or parenteral administration, such as, for example, pharmaceutically acceptable solvents, gelatin, gum arabic, lactose, starch, magnesium stearate, talc, vegetable oils, polyalkylene glycols, vaseline and the like.

The pharmaceutical products can be in a solid form, for example as tablets, coated tablets, suppositories, capsules and the like, or in a liquid form, for example as solutions, suspensions or emulsions. If appropriate, they are sterilized and contain auxiliaries, such as preservatives, stabilizers or emulsifying agents, salts for modifying the osmotic pressure and the like.

In particular, pharmaceutical products can contain the compounds according to the invention in combination with other therapeutically useful substances. The compounds according to the invention can be formulated to combination products with these, together with the abovementioned auxiliaries and/or excipients.

The following examples illustrate the invention in more detail:

EXAMPLE 1

10.0 g (0.053 mol) of thieno(2,3-d)-1,2-thiazol-3(2H)-one 1,1-dioxide are suspended in 100 ml of dry dimethylformamide, 2.54 g (0.053 mol) of a 50% strength sodium hydride suspension washed with benzene are added, the solid is dissolved at 70° C., while stirring (10 minutes), the solution is cooled to 30° C., 12.16 g (0.058 mol) of 1,1-dimethylethyl 3-bromopropionate are added and the mixture is heated at 100° C. for 3 hours. It is then evaporated in vacuo, the residue is partitioned between $NaHCO_3$ solution and $CH_2Cl_2$ and the organic phase is separated off, dried with $Na_2SO_4$ and evaporated. The crystalline residue, which consists of 1,1-dimethylethyl-2,3-dihydro-3-oxo-thieno-(2,3-d)-1,2-thiazole propionate 1,1-dioxide can be recrystallized from diisopropyl ether.

Yield: 11 g (65.5%).

Melting point (diisopropyl ether): 66°–67° C. of colorless crystals.

EXAMPLE 2

10.0 g (0.053 mol) of thieno(3,2-d)-1,2-thiazol-3(2H)-one 1,1-dioxide are suspended in 100 ml of dry dimethyl sulfoxide and reacted at 95° C. for 4 hours in a manner analogous to that described in Example 1. 1,1-dimethylethyl-2,3-dihydro-3-oxo-thieno(3,2-d)-1,2-thiazole propionate 1,1-dioxide is obtained in a yield of 67%.

Melting point (diisopropyl ether): 72°–74° C.

EXAMPLE 3

10 g (0.053 mol) of thieno(3,4-d)-1,2-thiazol-3(2H)-one 1,1-dioxide are suspended in 100 ml of dry dimethylacetamide and reacted at a reaction temperature of 110° C. for 3 hours in a manner analogous to that described in Example 1. 1,1-dimethylethyl-2,3-dihydro-3-oxo-thieno(3,4-d)-1,2-thiazole propionate 1,1-dioxide is obtained in a yield of 62%.

Melting point (diisopropyl ether): 94°–95° C.

EXAMPLE 4

10 g (0.045 mol) of 5-chloro-thieno(3,2-d)-1,2-thiazol-3(2H)-one 1,1-dioxide are reacted with 10.03 g (0.048 mol) of 1,1-dimethylethyl 3-bromopropionate in a manner analogous to that described in Example 1. 1,1-Dimethylethyl-5-chloro-2,3-dihydro-3-oxo-thieno(3,2-d)-1,2-thiazole propionate 1,1-dioxide is obtained in a yield of 60%.

Melting point (diisopropyl ether): 115°–116° C.

EXAMPLE 5

A solution of 2.12 g (0.053 mol) of sodium hydroxide in 150 ml of water are added to 10 g (0.053 mol) of thieno(2,3-d)-1,2-thiazol-3(2H)-one and the mixture is stirred until a solution which is virtually free from residue is obtained. Small amounts of undissolved constituents are filtered off and the dry residue is prepared by evaporating off the water in vacuo. The alkali metal salt thus obtained is finely powdered and dried to constant weight under a high vacuum. This salt is suspended in 100 ml of dry dimethylformamide and dissolved at 80° C., while stirring, the solution is cooled to 30° C., 7.92 g (0.058 mol) of ethyl 3-chloropropionate are added and the mixture is heated at 100° C. for 4 hours 15 minutes.

The reaction mixture is worked up as descried in Example 1. Ethyl 2,3-dihydro-3-oxo-thieno(2,3-d)-1,2-thiazole-propionate 1,1-dioxide is obtained in a yield of 65%.

Melting point (diisopropyl ether): 62°–63° C.

EXAMPLE 6

A solution of 3.61 g (0.053 mol) of sodium ethylate in 120 ml of dry ethanol is added to 10 g (0.053 mol) of thieno(3,2-d)-1,2-thiazol-3(2H)-one and the mixture is stirred until a clear solution is obtained. The dry residue is prepared by evaporating off the solvent in vacuo. The sodium salt thereby obtained is finely powdered, dried to constant weight, subsequently suspended in 100 ml of dry dimethylformamide and dissolved at 80° C., while stirring, the solution is cooled to 30° C. and 10.49 g (0.058 mol) of ethyl 3-bromopropionate are added. The mixture is heated at 100° C. for a further 3 hours to bring the reaction to completion.

The reaction mixture is worked up as described in Example 1. Ethyl 2,3-dihydro-3-oxo-thieno(3,2-d)-1,2- thiazole-propionate 1,1-dioxide is obtained in a yield of 60%.

Melting point (diisopropyl ether): 95°–96° C.

EXAMPLE 7

10 g (0.053 mol) of thieno(3,4-d)-1,2-thiazol-3(2H)-one 1,1-dioxide are suspended in 100 ml of dry dimethylacetamide and treated with sodium hydride in a manner analogous to that described in Example 1, and the mixture is reacted with 10.49 g (0.058 mol) of ethyl 3-bromopropionate at 110° C. for 2 hours 40 minutes. Ethyl 2,3-dihydro-3-oxo-thieno(3,4-d)-1,2-thiazole propionate 1,1-dioxide is obtained in a yield of 65%.

Melting point (diisopropyl ether): 105°–107° C.

EXAMPLE 8

10.8 g of 1,1-dimethylethyl 2,3-dihydro-3-oxo-thieno(2,3-d)-1,2-thiazole-propionate 1,1-dioxide are dissolved in 110 ml of dry toluene, 113 mg of p-toluenesulfonic acid are added and the reaction mixture is heated under reflux for 90 minutes. After cooling, colorless crystals consisting of 2,3-dihydro-3-oxo-thieno(2,3-d)1,2-thiazole-propionic acid 1,1-dioxide are filtered off with suction and recrystallized from ethanol.

Yield: 79%

Melting point: 133°–135° C.

EXAMPLE 9

2,3-Dihydro-3-oxo-thieno(3,2-d)-1,2-thiazolepropionic acid 1,1-dioxide are obtained in a yield of 85% by reaction, analogously to Example 8, of 1,1-dimethylethyl 2,3-dihydro-3-oxo-thieno(3,2-d)-1,2-thiazole-propionate 1,1-dioxide in 120 ml of dry benzene while heating under reflux.

Melting point (water): 140°–142° C.

EXAMPLE 10 10.8 g of 1,1-dimethylethyl 2,3-dihydro-3-oxothieno(3,4-d)-1,2-thiazole-propionate 1,1-dioxide are dissolved in 100 ml of dry toluene, 110 mg of benzenesulfonic acid are added and the reaction mixture is heated under reflux for 95 minutes.

2,3-Dihydro-3-oxo-thieno(3,4-d)1,2-thiazole-propionic acid 1,1-dioxide is obtained in a yield of 78%.

Melting point (water): 173°–176° C.

EXAMPLE 11

8 g of 1,1-dimethylethyl 5-chloro-2,3-dihydro-3-oxo-thieno(3,2-d)-1,2-thiazole-propionate 1,1-dioxide are dissolved in 90 ml of dry toluene, 95 mg of methanesulfonic acid are added and the reaction mixture is heated at 115° C. for 105 minutes, while stirring.

5-Chloro-2,3-dihydro-3-oxo-thieno(3,2-d)-1,2-thiazole-propionic acid 1,1-dioxide are obtained in a yield of 82%.

Melting point (ethanol): 195°–197° C.

What we claim is:

1. A thieno-1,2-thiazole compound of the formula

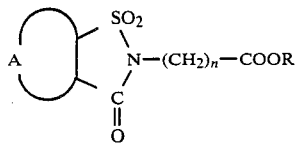

wherein A, with the two carbon atoms of the thiazole ring, forms a group of the formula

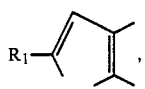

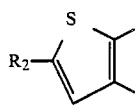

or

and the broken line indicates the double bond present in the thieno structures of the formulae IIa and IIb, n denotes the integer 2, 3 or 4, R denotes hydrogen or lower alkyl, $R_1$ denotes hydrogen, lower alkyl, halogen, trifluoromethyl, lower alkoxy or lower alkylthio and $R_2$ denotes hydrogen, lower alkyl or halogen; and the pharmaceutically acceptable salts of compounds of the formula I wherein R denotes hydrogen.

2. The compounds of the formula I defined in claim 1, wherein A denotes the group of the formula IIc.

3. The compounds according to claim 1, wherein n denotes the number 2.

4. The compounds according to claim 1, wherein R denotes 1,1-dimethylethyl or ethyl.

5. The compounds according to claim 1, wherein R denotes hydrogen, and pharmaceutically acceptable salts thereof.

6. A pharmaceutical composition for lowering blood lipids which comprises a compound according to claim 1, or a pharmaceutically acceptable salt thereof, in combination with a pharmaceutical acceptable carrier.

* * * * *